United States Patent [19]
Kambara et al.

[11] Patent Number: 5,730,850
[45] Date of Patent: Mar. 24, 1998

[54] CAPILLARY ARRAY ELECTROPHORESIS SYSTEM

[75] Inventors: Hideki Kambara, Hachioji; Satoshi Takahashi, Kunitachi; Takashi Anazawa, Kokubunji; Takashi Yamada, Tokyo; Yoshinobu Kohara, Kokubunji, all of Japan

[73] Assignee: Hitachi, Ltd., Tokyo, Japan

[21] Appl. No.: 588,776

[22] Filed: Jan. 19, 1996

Related U.S. Application Data

[63] Continuation-in-part of Ser. No. 337,412, Nov. 7, 1994, Continuation of Ser. No. 51,324, Apr. 23, 1993.

[30] Foreign Application Priority Data

Jan. 19, 1995 [JP] Japan .................................. 7-006264

[51] Int. Cl.$^6$ .......................... G01N 27/26; G01N 27/447
[52] U.S. Cl. ............................................. 204/603; 204/452
[58] Field of Search ...................................... 204/603, 452

[56] References Cited

U.S. PATENT DOCUMENTS

| | | | |
|---|---|---|---|
| 5,366,608 | 11/1994 | Kambara | 204/603 |
| 5,414,508 | 5/1995 | Takahashi et al. | 204/603 X |
| 5,439,578 | 8/1995 | Dovichi et al. | 204/603 |
| 5,498,324 | 3/1996 | Yeung et al. | 204/452 |
| 5,516,409 | 5/1996 | Kambara | 204/603 |

*Primary Examiner*—Kathryn L. Gorgos
*Assistant Examiner*—John S. Starsiak, Jr.
*Attorney, Agent, or Firm*—Antonelli, Terry, Stout & Kraus, LLP

[57] ABSTRACT

A capillary array electrophoresis system by which measurement is conducted using a large number of capillaries. The electrophoresis system includes a plurality of capillary array sheets stacked one on top of another wherein end portions of the capillaries at a detection region are arranged two-dimensionally in such a manner as to elute two-dimensionally a sample from the distal end of each capillary. Excitation light is applied to the sample eluted into a buffer solution, and a two-dimensional fluorescent image is picked up by a detector.

58 Claims, 6 Drawing Sheets

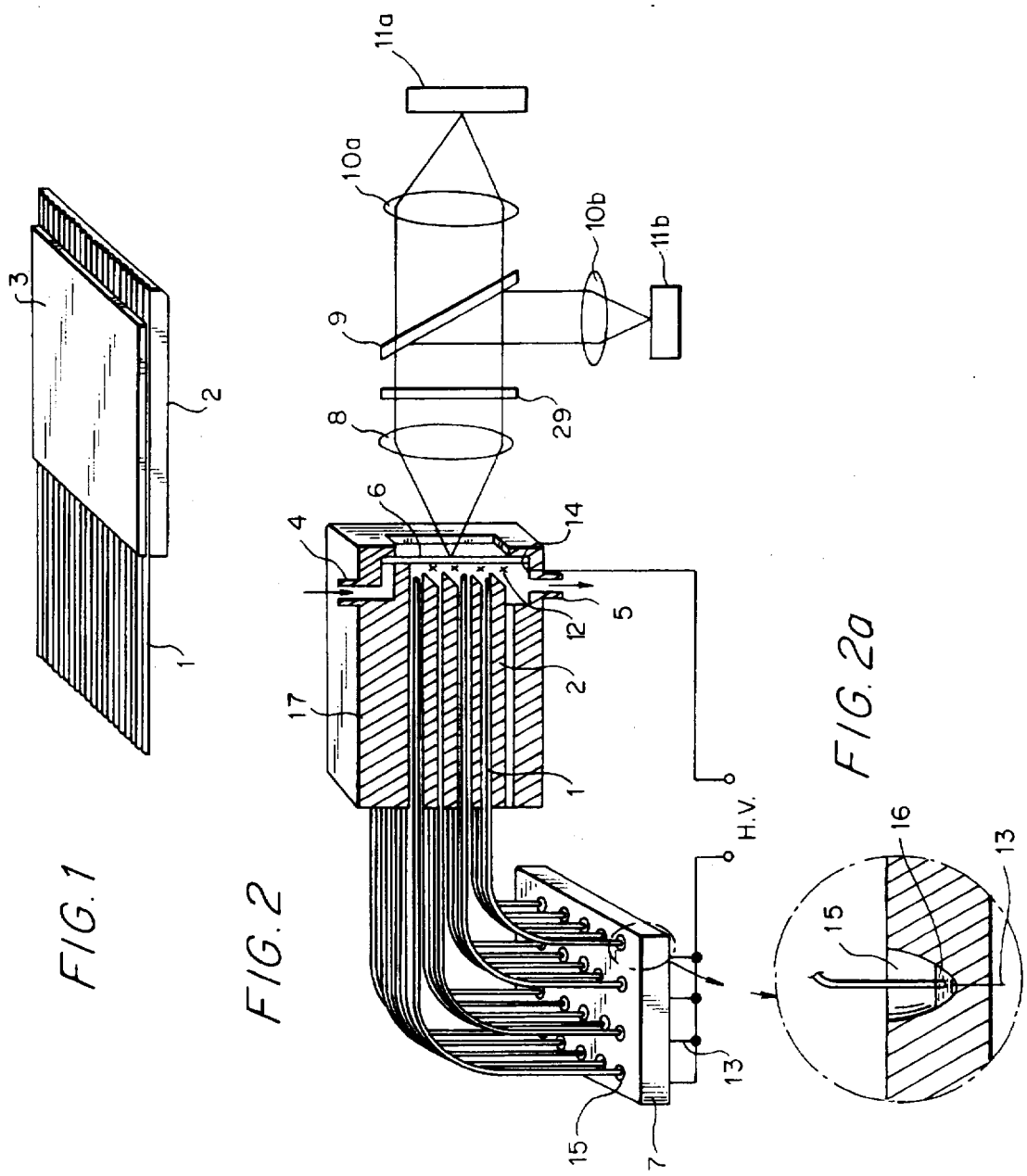

CAPILLARY ARRAY ELECTROPHORESIS SYSTEM

CROSS REFERENCE TO RELATED APPLICATIONS

This application is related to application Ser. No. 08/337,412 filed Nov. 7, 1994 which is a continuation of application Ser. No. 08/051,324 filed Apr. 23, 1993 the disclosures of which are incorporated herein by reference.

BACKGROUND OF THE INVENTION

This invention relates to an electrophoresis system. More particularly, the present invention relates to a capillary array electrophoresis system which is suitable for analysis of fluorophore-tagged DNAs and organic compounds.

As the need for DNA sequencing has increased there has been a tremendous desire for the development of high speed high through-put DNA sequencers and DNA analyzers. Fluorescence detection type electrophoresis systems using a slab gel as a separation medium have been conventionally used for DNA sequencing or DNA analysis. When the slab gel is used, however, there is a limit in increasing the analysis speed and through-put. Recently, a capillary array electrophoresis system which is more suitable for obtaining a high speed high through-put system by aligning a large number of capillaries filled with gel has been proposed (Nature 359, 167–168, 1992, Nature 361, 565–566, 1993).

In the capillary array electrophoresis system, the capillaries in the array at a measurement portion are aligned in line and are irradiated with light. Fluorescence emitted from the fluorophore-tagged DNA or organic compound is detected by scanning a detector relative to the capillaries, the detector being equipped with a photomultiplier with respect to the capillary arrays or by forming fluorescent spot images aligned in line on a detector by using a line sensor or an area sensor in combination with an imaging lens.

Because the number of capillaries in a capillary array greatly affects the overall through-put, it is very effective to increase the number of capillaries in the array for improving the throughput. However, from a practical aspect such as handling, the maximum number of capillaries is 50 to 100.

The system, in which the detector moves relative to the capillaries, uses a confocal fluorescence detection system in order to eliminate background fluorescence from the capillaries. Therefore, the distance between the detector and the portion to-be-measured must be kept highly accurate during the scanning. In consequence, the scanning speed cannot be increased so easily, and the number of capillaries that are measured at one time is estimated as about 50.

On the other hand, in the system which uses an imaging device such as a line sensor with a lens, the samples eluted from the capillaries aligned in line are simultaneously irradiated and detected. Therefore, unlike the scanning system described above, the problem of the scanning speed does not exist in the imaging system. However, when the length of the fluorescence emitting region is long, which is in proportion to the number of capillaries, a reduced image must be formed on the detector which results in a drop of collected fluorescence. Ordinarily, the length of the detector is 16 to 24 mm, a capillary diameter is about 0.2 mm and the intervals of the centers of the capillaries are about 0.4 mm. To avoid sensitivity loss due to low fluorescence detecting efficiency, an image magnification should be at least about ½ and the number of capillaries that can be used in such a system is limited to a range of 80 to 120 capillaries.

SUMMARY OF THE INVENTION

An object of the present invention is to provide a capillary array electrophoresis system by which measurement is made using a greater number of capillaries.

The above described object is accomplished by disposing two-dimensionally the end portions of capillaries in a detection region, causing a sample to elute from the end of each capillary into a two-dimensional plane, irradiating the sample with light and receiving a two-dimensional fluorescence image by an area sensor from a direction facing to the cross-sections of the capillary ends.

In other words, the capillary array electrophoresis system according to the present invention particularly provides an electrophoresis system which includes a plurality of capillary electrophoresis tracks, wherein the end portions of the capillary electrophoresis tracks are arranged two-dimensionally in a plane, an excitation light which irradiates samples separated in each capillary electrophoresis track, and a two-dimensional detector for simultaneously detecting fluorescence resulting from irradiation of the samples by the excitation light. The capillaries are filled with gel or the like, and the excitation light irradiates the samples eluted from the capillaries into the flow of the buffer solution.

The system preferably further includes apparatus for applying excitation light in parallel with the plane described above in a state that end portions of the plurality of capillaries are positioned on substantially the same plane almost perpendicular to the capillary tubes at the terminus portion, and apparatus for forming a two-dimensional fluorescence image from a direction vertical to the plane described above and detecting the image.

For the fluorescence detection of the samples, the samples are eluted in a flow of the buffer solution formed between the plane defined by the end portions of a plurality of capillaries and an optical window so placed as to face the plane and the detectors, and the samples are irradiated by excitation light to emit fluorescence. Alternatively, the samples can be irradiated after being eluted from the capillary ends in a sheath flow flowing in a direction of the extension of the axes of the capillaries. In this case, excitation light irradiates the sample passing through the plane substantially parallel to the plane which is defined by the end portions of a plurality of capillaries.

More concretely, a capillary array electrophoresis system according to the present invention includes an optical cell including a buffer solution, an optical window in contact with a buffer solution and capillary array sheets on which end portions of a plurality of capillaries are aligned at predetermined intervals and fixed to a holder, an excitation light and a fluorescence detection system. The capillary array sheets are stacked in such a manner that the distal ends of the capillaries face the optical window. A buffer solution is caused to flow in a space between the distal ends of the capillaries and the optical window in the direction of the stack of the capillary array sheets. The excitation light irradiates along each of the capillary array sheets in such a manner as to cross the flow of a sample eluted from the capillary array into the buffer solution, and the fluorescence detecting system detects fluorescence emitted from the sample by a two-dimensional detector through the optical window of the optical cell. The end portion of the holder facing the optical window is preferably chamfered at the corners of the surface opposite the surface on which the capillaries are disposed.

Another embodiment of capillary array electrophoresis system according to the present invention includes an optical cell including a buffer solution, an optical window in contact with a buffer solution and capillary array sheets on which end portions of a plurality of capillaries aligned at predetermined intervals are clamped by an upper holder and a lower holder, an excitation light irradiation system and a fluorescence detecting system. The capillary array sheets are stacked one on top of another. Each of the upper and lower holders of each capillary array sheet has a flat end surface and an edge portion protruding from the end surface and has a buffer solution flow path opening to the end surface. The edge portion of the holders are in contact with the optical window to make a space isolated for each of the capillary sheets. The excitation light irradiation system applies excitation light to the space separated for each of the capillary array sheets, and the fluorescence detecting system detects fluorescence emitted from samples by a two-dimensional detector through the optical window of the optical cell. The opening in the end surface of the buffer solution flow path of the upper holder communicates with the buffer solution inlet of the optical cell, and is preferably positioned on a substantial intermediate line of adjacent capillaries.

Another embodiment of the capillary array electrophoresis system according to the present invention includes an optical cell including a buffer solution inlet, a buffer solution outlet, a partition having a plurality of parallel slits disposed between the buffer solution inlet and the buffer solution outlet, an optical window disposed substantially parallel to the partition with a predetermined gap and in contact with a buffer solution, capillary array sheets on which end portions of a plurality of capillaries are aligned at predetermined intervals and are fixed to a holder, an excitation light irradiation system and a fluorescence detecting system. The capillary array sheets are stacked one on top of another while the distal ends of the capillaries are inserted into the slits of the partition. The buffer solution flows from the buffer solution inlet in the axial direction of the capillaries through the slits of the partition, then passes through a space between the partition and the optical window and goes out from the buffer solution outlet. The excitation light goes through along the slits of the partition, and the fluorescence detecting system detects fluorescence emitted from a sample by a two-dimensional detector through the optical window of the optical cell.

Excitation light can pass along the slits of the partition. The capillary array sheets are clamped by upper and lower holders each having grooves for causing the buffer solution to flow therethrough in the surface, and the distal end portions of the upper and lower holders can be inserted into the slits of the partition. The grooves for passing the buffer solution may be formed in the holder insertion surface of the partition instead of the holder of the capillary array sheets.

The size of a fluorescence image can be greatly reduced by arranging the end portions of the capillary arrays two-dimensionally but not linearly. When, for example, two-hundred capillaries are aligned at 0.4 mm pitch, the total length is 80 mm, but when the same number, that is, 200, of capillaries are arrayed in four sheets which are stacked at 1 mm pitch, and in eight sheets which are stacked at the same pitch, the image sizes are 4 mm×20 mm and 8 mm×10 mm, respectively, and accordingly the lengths of image are smaller. In order words, fluorescence detection can be made with a large fluorescence collecting angle and therefore a high collecting efficiency.

Because the capillaries are disposed two-dimensionally, the number of capillaries in one capillary array sheet can be small and their handling is easier. The handling of the capillaries becomes even easier by using the capillary array sheet fixed on the holder and stacking such array sheets into a plurality of stages to form a two-dimensional capillary array. Because positional accuracy of the capillaries can also be improved by stacking the array sheets, irradiation with excitation light can be carried out efficiently.

Because the samples eluted from the capillaries are carried by the flow of the buffer solution, the samples eluted from a plurality of capillaries can be detected without mutual interference although the capillaries are arranged two-dimensionally. The flow of the buffer solution is set in the axial direction of the capillaries and excitation light irradiates a position before each flow carrying the samples is mixed. Alternatively, the buffer solution flows inside the space separated for each capillary array sheet and excitation light is applied. In this way, mutual interference of the samples eluted from a plurality of capillaries can be completely prevented. When the buffer solution flows in a direction perpendicular to the axes of the capillaries, mutual interference of the samples eluted from the capillaries can be avoided by setting wide intervals between the capillary array sheets or by making a dead volume, between the adjacent capillary array sheets, so as to promote diffusion and dilution of the samples.

BRIEF DESCRIPTION OF THE DRAWINGS

The present invention will be more apparent from the following detailed description, when taken in conjunction with the accompanying drawings, in which:

FIG. 1 is a perspecitve view showing an example of a capillary array sheet of the present invention;

FIGS. 2 and 2a are explanatory views of a two-dimensional capillary array electrophoresis system of the present invention;

DETAILED DESCRIPTION OF THE PREFERRED EMBODIMENTS

Figure 3:
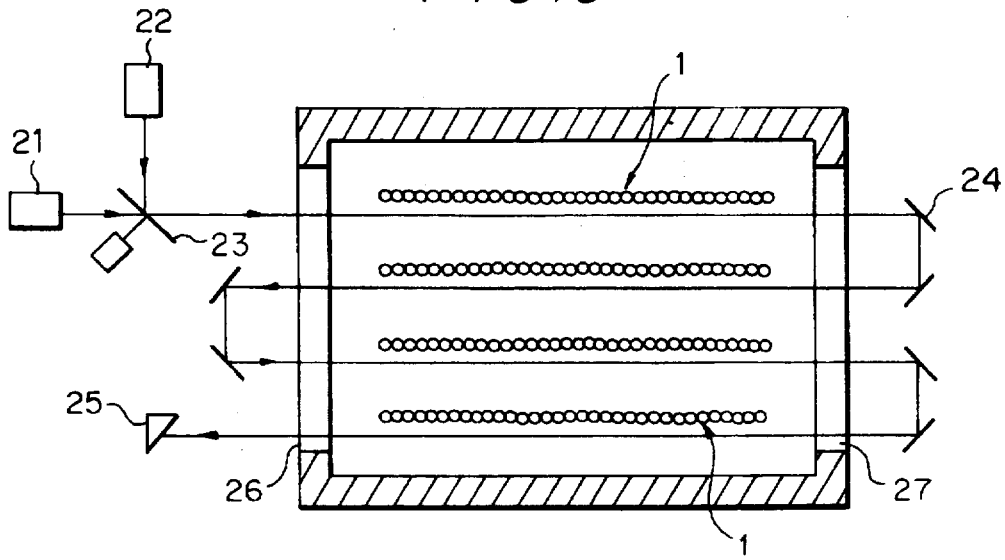
FIG. 3 is an explanatory view showing an example of a fluorescence excitation-light irradiation system.
Figure 4:
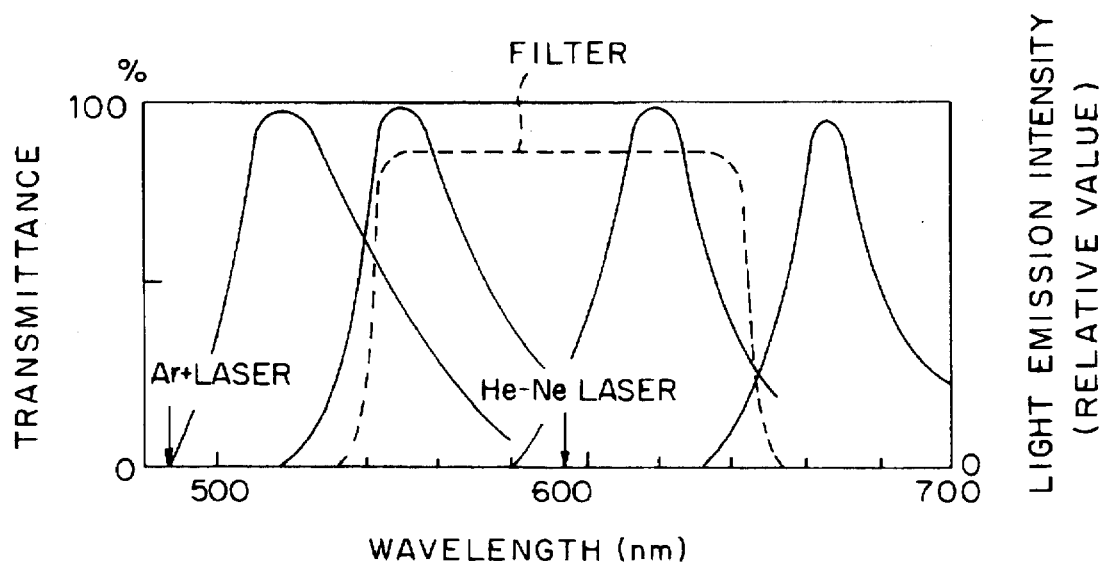
FIG. 4 is a diagram showing light emission intensity and transmittances of a fluorophore and a dichroic mirror.

Hereinafter, the present invention will be explained in detail with reference to features of the present invention forming various embodiments of the present invention as illustrated in FIGS. 1–15.

FIG. 1 shows a first embodiment of a capillary array sheet 1 formed by aligning a large number of capillaries and retaining them in a sheet form. Each capillary is made of quartz and has an inside diameter of 0.1 mm and an outside diameter of 0.2 mm. The length of each capillary is 30 cm, and a polyacrylamide gel (5% T, 4% C) is charged in the capillary. The composition of the gel inside the capillary can be changed in various ways depending on the application. The distal end portions of twenty-four capillaries on the right side are aligned and held by a capillary holder 2 made of a 1.5 mm-thick stainless steel sheet, and a 0.1 mm-thick polyethylene terephthalate capillary array cover 3 is placed on the holder 2 and is bonded to the cover 3. The corners of the surface opposite to the capillary holding surface at the distal end portion of the capillary holder 2 are chamfered as shown in the drawing.

FIG. 2 is a schematic view of a capillary array electrophoresis system produced by stacking a plurality of capillary array sheets shown in FIG. 1 into a two-dimensional array. The capillary array sheets 1 held by the capillary holders 2 are stacked into four stages at intervals of 3 to 5 mm inside an optical cell 17 and are fixed in such a manner that the distance between the distal end portions of the capillaries and a quartz window 6 for fluorescence detection is from about 0.2 mm to about 0.3 mm. A buffer solution inlet 4 is defined at the upper portion of the optical cell 17, and a buffer solution flows from above to below inside the space between the distal end portions of the capillary sheets and the quartz window 6 for fluorescence detection at a linear velocity of about 0.1 to about 0.5 mm/sec and flows out from a buffer solution outlet 5 disposed at the lower portion of the optical cell. An electrode 14 is disposed in a buffer solution flow path.

DNA fragments labeled with various fluorophores are held in sample wells 15 of a titer plate 7 having 96 holes, and each fragment is injected electrophoretically into each capillary of the capillary array. As shown in enlargement in the circle of FIG. 2, electrophoretical injection is carried out by placing a sample injection end of the capillary array into each well 15 of the titer plate 7 and applying a voltage of 8 kV for about 5 seconds between the sample 16 and the other end of the capillary through an electrode 13 disposed at the bottom of the well 15 and an electrode 14 disposed in the optical cell 17. The electrode on the sample side may be inserted from above the titer plate into the sample well 15 together with the sample injection end of the capillary without fixing it to the bottom of the sample well 15.

After the injection of the sample, the sample injection end of the capillary is taken out from the titer plate and is immersed into the buffer solution, not shown, and a voltage of about 5 kV is applied between the electrode immersed in the buffer solution and the electrode 14 of the optical cell 17 so as to create an electric field of 100 V/cm to 200 V/cm. The DNA fragments migrate inside the capillary from the left side to the right side in the drawing, and the DNA fragments separated in accordance with their lengths are eluted from the right ends of the capillaries into the buffer solution of the optical cell 17 and then move down while being carried by the flow of the buffer solution.

Laser beams are applied to the buffer solution path between the capillary holder 2 and the quartz window 6 for fluorescence detection from a direction orthogonal to the liquid flow (direction crossing the sheet of the drawing in FIG. 2) as shown in FIG. 3. The laser beams outgoing from two laser beam sources 21, 22 having mutually different emission wavelengths are caused to alternately pass through the same optical path by a chopping wheel 23 having alternately light reflection portions and light transmission portions. The laser beams pass through light transmission windows 26, 27 provided in the sides of the optical cell 17, are then turned back by an optical member 24 for difracting light such as a gold evaporated mirror or prism, pass through portions located 0.5 to 1 mm below each capillary array 1 and are finally absorbed by an optical trap 25.

The laser beam passing below each capillary array 1 excites the DNA labeled with a fluorophosphore at a laser irradiation portion 12 designated by symbol X in FIG. 2 and generates fluorescence. The fluorescence generated from the labeled fluorophosphore is collected by a lens 8, passes through a filter 29 for cutting out the excitation light and is separated according to the wavelength by a dichroic mirror 9. Images are formed on two-dimensional detectors 11a, 11b by lenses 10a, 10b.

The DNA fragments eluted from the capillary array are carried by the flow of the buffer solution and then pass in front of the end portions of other capillary arrays. However, because the DNA fragments are diffused in the buffer solution and are sufficiently diluted before they reach the position in front of the adjacent capillary array, they do not hinder the detection of the DNA fragments eluted from the adjacent capillary array. The buffer solution staying in the space defined by the chambered portions of the capillary holder 2 assists this diffusion and dilution of the DNA fragments eluted.

In DNA sequencing, the DNA fragments are labeled with four different kinds of fluorophores in accordance with A (adenine), C (cytosine), G (guanine) and T (thymine) of the base species at 3' terminus, and measurement is made by wavelength separation. Although there are various fluorescence detection methods with wavelength separation, a method in which an Ar+ laser beam having a wavelength of 488 nm and a He-Ne laser beam having a wavelength of 594 nm are alternately applied and a dichroic mirror 9 having transmission wavelength characteristic shown in FIG. 4 and two-dimensional detectors 11a, 11b are used. "FITC" (fluorescein isothiocyanate, emission wavelength of approx. 520 nm), "JOE" (trade name, emission wavelength of approx. 545 nm), "Sulforhodamine 101" (emission wave length of approx. 615 nm) and "Cy-5" (trade name, emission wavelength of approx. 667 nm) are used as te labeling fluorophores. Hereinafter, they will be referred to as "F1", "F2" "F3" and "F4" from the shorter wavelength side of the emission wavelengths.

The fluorophores F1 and F2 can be efficiently excited by an Ar+ laser, and the fluorophores F3 and F4 are excited by an He-Ne laser. On the other hand, the dichroic mirror 9 transmits the fluorescence from F2 and F3 and mainly reflects the beams emitted from F1 and F4. Therefore, the beam from F1 is directed to the detector 11b and the beam from F2, to the detector 11a, during the irradiation with an Ar' laser beam. The beam from F4 is directed to the detector 11b and the beam from F3, to the detector 11a, during the irradiation with an He-Ne laser. A filter 29 for cutting out the excitation beam, disposed in a light reception optical path, can be a color glass filter which cuts out a beam of a wavelength of 488 nm and transmits the beams on a longer wavelength side and a notch filter which cuts out the He-Ne laser beam. In this way, the DNA fragments eluted from each capillary of the capillary array can be separated and detected.

A light emitting diode array, a laser diode array, etc, can be used as the excitation beam source. In this case, the optical path need not be folded by a reflecting mirror, or the like. When a high intensity laser beam source is used, the laser beam may be sequentially split into a plurality of parallel laser beams by using a plurality of beam splitters.

Besides the excitation beam irradiation method and the fluorescence detection method described above, known arbitrary methods can of course be employed.

Figure 5:
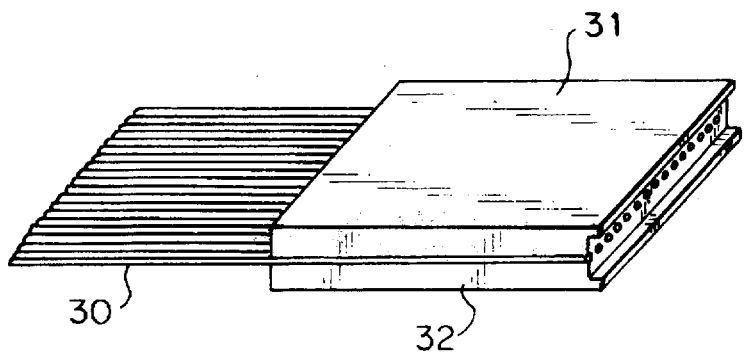
FIG. 5 is a perspective view showing another example of the capillary array sheet of the present invention.
Figure 6:
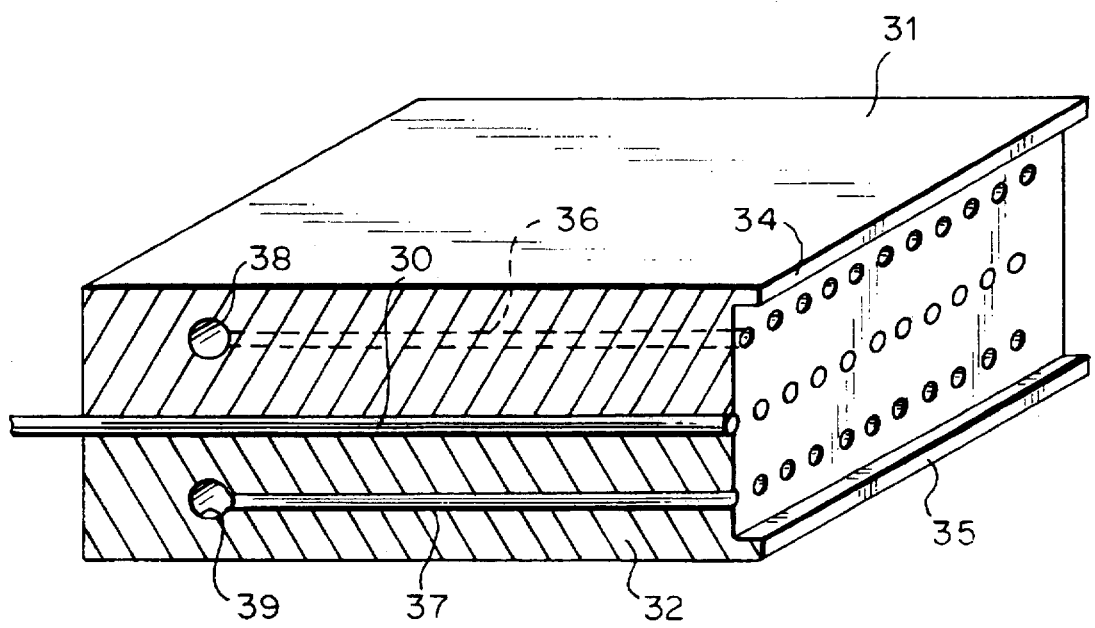
FIG. 6 is a detailed explanatory view of the capillary array sheet shown in FIG. 5.

FIGS. 5 and 6 show a second embodiment of a capillary array sheet. As shown in FIG. 5 which is an overall perspective view, the capillary array sheet 30 in this embodiment is produced by aligning and holding forty capillaries each having an inside diameter of 0.1 mm and an outside diameter of 0.2 mm between two capillary holders 31 and 32 made of stainless steel and having a thickness of 2 mm, at a pitch of 0.4 mm. Referring to FIG. 6 which shows the distal end portion in enlargement, the end face of each holder 31, 32 has a protruding edge portion 34, 35, and the distal end portion of the capillary array 30 is exposed from a groove-shaped portion sandwiched between these two protruding edge portions 34, 35. Lines of holes 36 and 37, each of which has a diameter of 0.2 mm and serves as a buffer solution flow path, are so dispose in the upper and lower holders 31, 32 as to open to the groove-shaped portion. The flow paths 36 provided in the upper holder 31 are all connected to one buffer solution inlet 38 formed in the direction of the arrangement of the capillary array inside the holder, and the flow paths 37 provided in the lower holder 32 all communicate likewise with one buffer solution outlet 39 formed in the direction of the arrangement of the capillary array.

Figure 7:
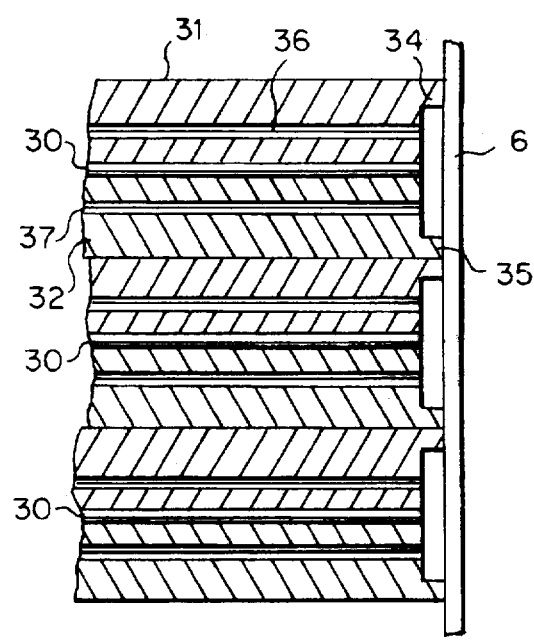
FIG. 7 is a partial enlarged view of an optical cell using the capillary array sheet shown in FIG. 5.

As shown in FIG. 7, in this embodiment, a plurality of capillary array sheets 30 of the invention are stacked in the optical cell in a state that the protruding edge portions of the end faces thereof are in close contact with the quartz window 6 for fluorescence detection. The DNA fragments labeled with various fluorophores respectively are electrophoretically injected into the sample injection ends of the capillary arrays, and migrate inside the capillaries when a voltage is applied between the electrode disposed in the buffer solution, in which the sample injection end is immersed, and the electrode disposed in the buffer bath for sheath flow. The DNA fragments eluted from the tip of each capillary array are carried by the flow of the buffer solution introduced from the buffer solution inlet 38 disposed in the upper holder 31 and flowing out from the buffer solution flow path 36. In the interim, the DNA fragments are irradiated with the laser beam travelling in the groove-shaped portion at the holder end portion by an excitation light irradiation system similar to the one shown in FIG. 3, and generate fluorescence. The fluorescence generated passes through the quartz window 6 of the optical cell and is measured by a fluorescence detecting optical system similar to that of Embodiment 1. After the measurement of fluorescence, the DNA fragments flow out from the buffer solution outlet 39 through the buffer solution flow paths 37 disposed in the lower holder 32.

Figure 8:
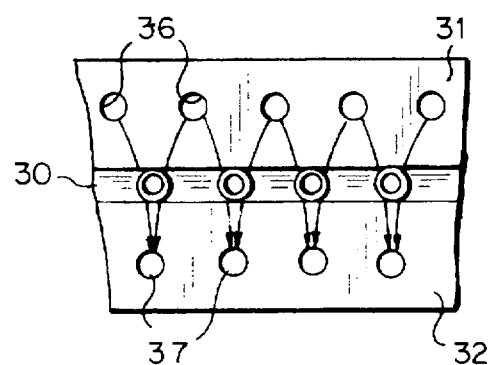
FIG. 8 is an explanatory view showing the flow of a buffer solution.

The positional relationship of the distal end of each capillary in the capillary array sheet 30 with the buffer solution flow paths 36 formed in the upper holder 31 and the buffer solution flow paths 37 formed in the lower holder 32 is as follows. As shown in FIG. 8, the outlet of each buffer solution flow path 36 is advantageously interposed between two adjacent capillaries and the inlet of each buffer solution flow path 37 is advantageously aligned with the position of each capillary. According to such an arrangement, the buffer solution flows out in such a manner as to spread from the hole 36, and the samples eluted from the capillaries are retained in the flow of the buffer solution spreading from both sides of the capillaries and are prevented from diffusing. Therefore, the samples can reach the laser irradiated portion while keeping a high concentration.

However, the arrangement shown in FIG. 8 is advantageous but is not always necessary, and the flow inlet and outlet may be disposed in alignment with the position of each capillary or may be disposed at random without alignment with the position of each capillary. Alternatively, a slitlike flow inlet or a slit-like flow outlet may be formed by connecting all the outlets of the flow paths 36 of the upper holder 31 or all the flow inlets of all the flow paths of the lower holder 32.

Further, only one of the protruding edges portions 34, 35 of the end face of the capillary array sheet 30 may work instead of providing the protruding edges for both of the upper and lower holders.

According to this embodiment, the DNAs eluted from a plurality of capillary array sheets can be simultaneously measured, avoiding completely the possibility of interference that a sample eluted from one capillary array sheet affects the detection of samples eluted from other capillary array sheets.

Figure 9:
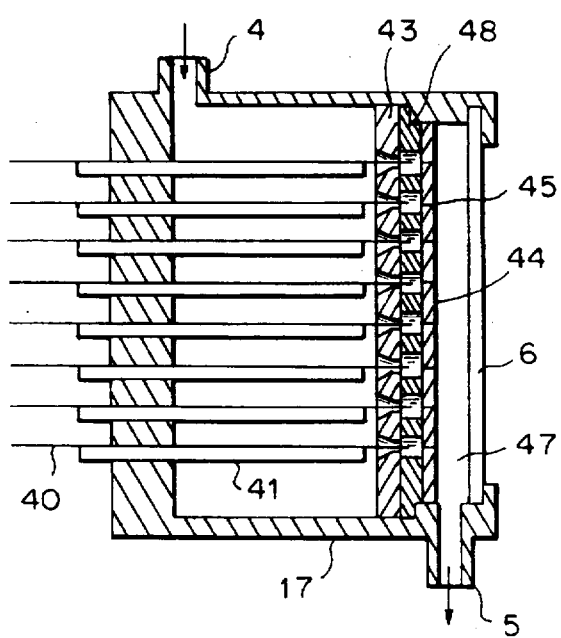
FIG. 9 is an explantory view of another emboiment of the two-dimensional capillary array electrophoresis system.
Figure 10:
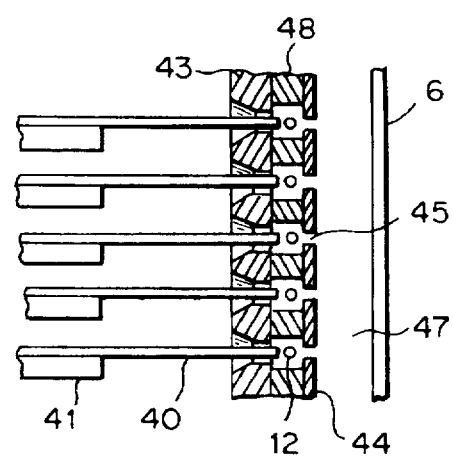
FIG. 10 is a partial enlarged view of FIG. 9.

Next, an embodiment of the present invention wherein a sheath flow of the buffer solution is formed in the direction of the axis of the capillary on the sample elution side will be explained. FIG. 9 is a schematic sectional view of a two-dimensional capillary array electrophoresis system according to this embodiment and FIG. 10 is a detailed view in the proximity of the right end portion of the capillary.

A capillary sheet 40 produced by aligning and holding forty capillaries each having an outside diameter of 0.2 mm and an inside diameter of 0.1 mm on a 1 mm-thick stainless steel capillary holder 41 at a 0.4 mm pitch is inserted into an optical cell 17. In this embodiment, eight capillary sheets are stacked at intervals of 0.5 mm. The sheet pitch is 1.5 mm. In other words, 320 capillaries are accommodated in a region of 16 mm×12 mm. The sheet pitch can be 0.5 mm and in such a case, 960 capillaries can be accommodated.

The each capillary end to protrude by a distance of 5 mm from the end portion of the capillary holder 41, and a capillary array cover is placed on the array to fix them with glue. The sheet-like capillary array is inserted into a slit 43' provided in a fixing plate 43 made of stainless steel. The slit has a width of 0.2 mm and a length of 16 mm and its entrance side for the capillary array is tapered so that the capillary array can be easily inserted.

A quartz intermediate plate 44 having a thickness of 0.3 mm is provided 1 mm apart from the ends of the capillaries. In the quartz intermediate plate 44, small holes 45 having a diameter of 0.2 mm or slits are provided at intersections of the extended lines of the capillaries. A 1 mm-thick quartz optical window 6 for fluorescence detection is 2 mm apart from this plate. The thickness of the capillary sheet inclusive of the capillary array cover is about 1.3 mm, and the sheath solution flows from the 0.2 mm gap between the sheets. The buffer solution flowing into the optical cell 17 from the buffer solution inlet 4 flows through the small holes 45 bored in the intermediate plate 44 into the region 47 and flows out from the buffer solution outlet 5. The intermediate plate 44 serves to form the sheath flow with each capillary being the axis.

In order to make the sheath flow smooth, quartz plates 48 for partitioning the sheets are disposed on the capillary end side between the sheets 40. Slits 49 are provided in the sheet partition quartz plates 48 at positions corresponding to the capillary array sheets. The quartz plate 48 and the fixing plate 43 described above may be made integrally with each other of a single quartz plate.

Figure 11:
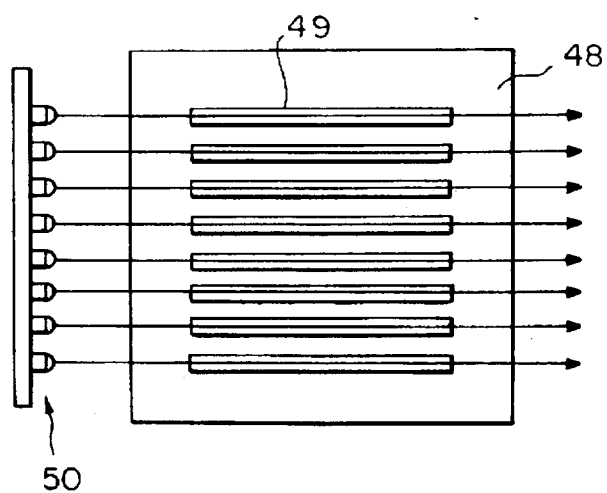
FIG. 11 is an explanatory view of a fluorescence excitation-light irradiation system using light emitting diode arrays.
Figure 12:
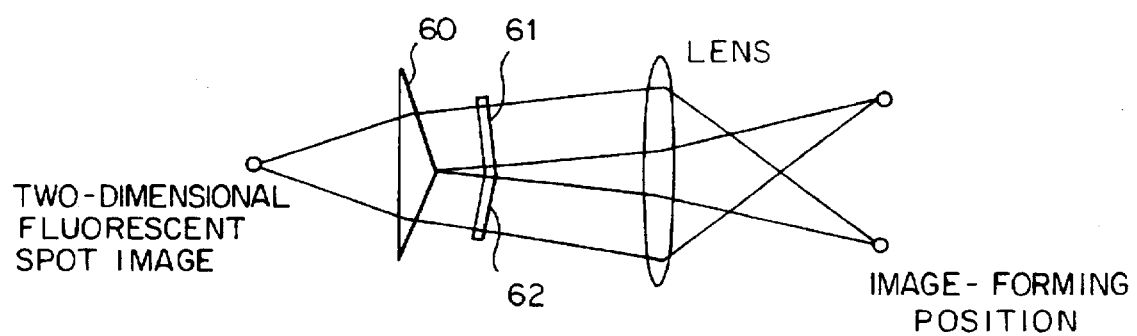
FIG. 12 is an explanatory view of a fluorescence detecting system using an image splitting prism.

Lasers are used as the excitation source, and the laser beams go through inside the slits 49 formed in the quartz plates 48 from the side of the optical cell. At this time, the laser beams are turned back by an optical system similar to the one shown in FIG. 3 whenever one capillary sheet is irradiated, and all the positions 12 shown by black circles in FIG. 10 and located in front of the elution side of the capillary array sheets 40 and spaced 0.5 to 1 mm apart therefrom are simultaneously irradiated. A light emitting diode array or a laser diode array may be used as the light source as shown in FIG. 11.

Fluorescent spot images arranged into a two-dimensional matrix can be obtained by the irradiation of the excitation beam and are detected by two two-dimensional detectors through the optical window 6 in the same way as in the foregoing embodiment. It is also possible to increase the gap between the capillary array sheets (1.5 mm in this embodiment), to form two-dimensional fluorescent spot images having deviated image focusing points by an image splitting prism 60 shown in FIG. 12, and to receive the images by one two-dimensional detector. Filters 61, 62 having suitable transmission wavelength bands are disposed on the optical path.

The optical cell 17 may be rotated by 90 as a whole so that the quartz window 20 faces down. In such a case, the seal at the capillary sheet inlets for preventing buffer leakage from the optical cell becomes easier.

Figure 13:
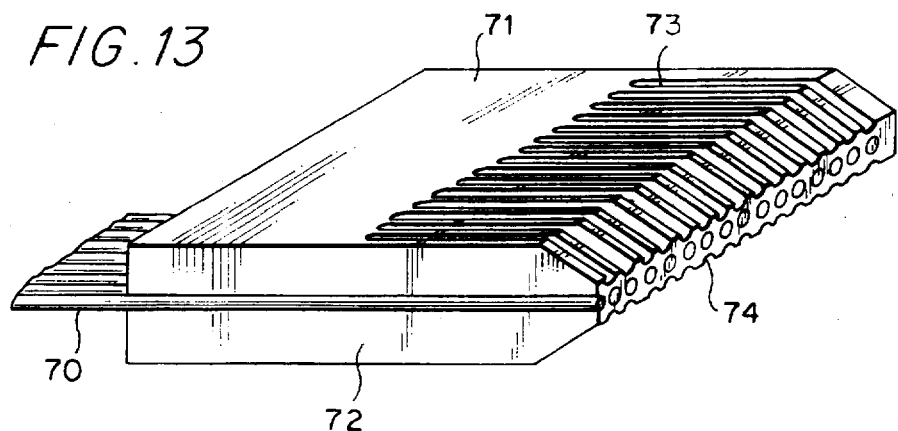
FIG. 13 is an explanatory view showing still another example of the capillary array sheet of the present invention.
Figure 14:
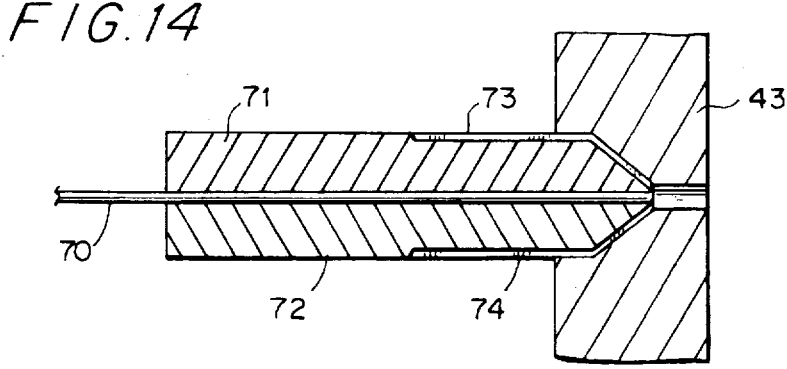
FIG. 14 is a partial enlarged view of an optical cell using the capillary array sheet shown in FIG. 13.

Though the end portions of the capillary arrays protrude from the capillary holder in the embodiment described above, the ends of the capillary arrays 70 may be sandwitched by two chamfered capillary holders 71 and 72 as shown in FIG. 13. The chamfered end portions of these capillary array sheets are inserted into and fixed to the grooves made in the fixing plate 43 as show in FIG. 14. According to this structure, because the end portions of the capillary array do not protrude, the possibility of crashing the capillaries during handling is low, also the assembly of the system is easier. The buffer solution flows through the grooves 73, 74 formed in the surface of the holder and flows into the slits 76 provided in the fixing plate 43. The buffer solution may be caused to flow through slits 76 through fine grooves provided in the surface of the fixing plate 43 instead of forming the grooves 73, 74 in the surface of the holder 71, 72.

The two-dimensional capillary array electrophoresis system according to the present invention is not limited to the improvement of the through-put by constituting a large number of capillaries into an array. It is biologically important to measure the distribution of m-RNA over a thin sliced tissue by hybridizing fluorophore-tagged DNA probe with m-RNA in the tissue. In this case, a fluorescence microscope has been exclusively used conventionally, but a large number of DNA probes must be detected simultaneously. The prior art technology observes several kinds of probes at most by changing the color taggs on the probes. If a large number of probe species can be distinguished by changing the lengths of the DNA probes, a large number of DNA probes can be simultaneously measured, and the present invention can be effectively utilized for such an application.

Figure 15:
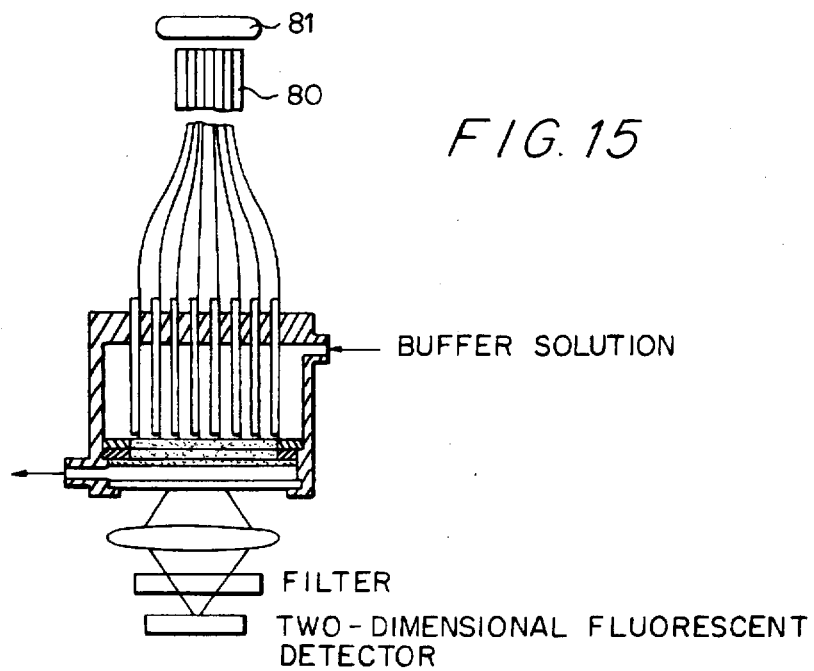
FIG. 15 is an explantory view of an apparatus for injecting DNA, etc., directly from a thin slice of tissue into capillaries and carrying out the measurement.

FIG. 15 shows an embodiment of the present invention for addressing the above described application. Unlike the foregoing embodiments, the capillary arrays 80 are held vertically. The upper portions of the capillaries each having an inside diameter of 0.1 mm and an outside diameter of 0.2 mm are arranged most densely. The lower portions of the capillaries are arranged in a similar shape, too, but the intervals are twice so as to measure and discriminate the fluorescent signals from the capillaries. A thin slice of tissue 81 hybridized with the DNA probe is placed in contact with the upper end faces of the capillaries, and DNA probes leaving from m-RNA in the tissue by raising temperature are electrophoretically injected into the capillaries 80. This electrophoretic injection is carried out by placing filter paper with the buffer solution on the slice of tissue 81, putting the electrode on this filter paper and applying a voltage between this electrode and the electrode provided in the buffer solution in which the lower end portions of the capillaries are immersed.

The DNA probes are injected into the capillaries close to the position where they are hybridized inside the tissue and are separated by gel electrophoresis. The lengths of the DNA probes are changed in accordance with their kinds, and their kinds can be identified from the electrophoresis times. The hybridization positions inside the tissue can be known from the position of the two-dimensional fluorescent image. The optical cell, the excitation-beam irradiation system and the fluorescent detecting system which have been all explained in the foregoing embodiments can be used.

Using this embodiment, the object which is distributed two-dimensionally can be measured, while keeping its two-dimensional distribution information. This can be applied to the distribution measurement of DNA collected on an oligo-chip on which the probes are arranged two-dimensionally.

According to the present invention, an extremely large number of capillaries are arranged into arrays and a large number of fluorophore-tagged DNAs can be analyzed without deteriorating the sensitivity. In other words, an extremely large number of fluorescent spot images can be detected without the drop of the sensitivity due to reduction of the images by arraying two-dimensionally the capillary arrays.

While the present invention has been described in detail and pictorially in the accompanying drawings it is not limited to such details since many changes and modifications recognizable to those of ordinary skill in the art may be made to the invention without departing from the spirit and the scope thereof.

We claim:

1. A capillary array electrophoresis system comprising:
   a plurality of capillary array sheets each having a plurality of capillary electrophoresis tracks having end portions which are aligned at selected intervals in a single row, and being fixed to a holder, wherein terminal ends of said plurality of capillary array sheets are stacked one on top of another;
   a light source emitting an excitation light which irradiates samples near said terminal ends; and
   a two-dimensional detector for detecting fluorescence emitted from said samples.

2. A capillary array electrophoresis system according to claim 1, wherein said samples are eluted into a flow of buffer solution and said excitation light irradiates said samples eluted in said buffer solution.

3. A capillary array electrophoresis system according to claim 1, wherein said plurality of capillary electrophoresis tracks are filled with a gel.

4. A capillary array electrophoresis system according to claim 1, wherein said terminal ends of said plurality of capillary electrophoresis tracks of each capillary array sheet lie on substantially the same plane, and wherein said system further comprises:
means for irradiating said excitation light in parallel with said plane; and
means for forming a two-dimensional fluorescence image from a direction perpendicular to said plane.

5. A capillary array electrophoresis system according to claim 2, wherein said terminal ends of said plurality of capillary electrophoresis tracks of each capillary array sheet lie on substantially the same plane, and
wherein said system further comprises:
means for irradiating said excitation light in parallel with said plane; and
means for forming a two-dimensional fluorescence image from a direction perpendicular to said plane.

6. A capillary array electrophoresis system according to claim 3, wherein said terminal ends of said plurality of capillary electrophoresis tracks of each capillary array sheet lie on substantially the same plane, and
wherein said system further comprises:
means for irradiating said excitation light in parallel with said plane; and
means for forming a two-dimensional fluorescence image from a direction perpendicular to said plane.

7. A capillary array electrophoresis system according to claim 2, wherein the flow of said buffer solution is formed between a plane formed by said terminal ends of said plurality of capillary electrophoresis tracks and a plate which is disposed opposite said plane, said plate having small holes or slits to permit the flow of said buffer solution from said terminal ends into said small holes or slits, wherein said samples are eluted into said buffer solution and are fluorescently detected.

8. A capillary array electrophoresis system according to claim 5, wherein the flow of said buffer solution is formed between a plane formed by said terminal ends of said plurality of capillary electrophoresis tracks and a plate which is disposed opposite said plane, said plate having small holes or slits to permit the flow of said buffer solution from around said terminal ends into said small holes or slits, wherein said samples are eluted into said buffer solution and are fluorescently detected, then flow out from the small holes or slits.

9. A capillary array electrophoresis system according to claim 2, wherein said buffer solution is caused to flow in an axial direction of said plurality of capillary electrophoresis tracks so as to form a sheath flow flowing in the axial direction of said capillary electrophoresis tracks, and said excitation light irradiates said sheath flow region.

10. A capillary array electrophoresis system according to claim 5, wherein said buffer solution is caused to flow in an axial direction of said plurality of capillary electrophoresis tracks so as to form a sheath flow flowing in the axial direction of said capillary electrophoresis tracks, and said excitation light irradiates said sheath flow region.

11. A capillary array electrophoresis system according to claim 7, wherein said buffer solution is caused to flow in an axial direction of said plurality of capillary electrophoresis tracks so as to form a sheath flow flowing in the axial direction of said capillary electrophoresis tracks, and said excitation light irradiates said sheath flow region.

12. A capillary array electrophoresis system according to claim 8, wherein said buffer solution is caused to flow in an axial direction of said plurality of capillary electrophoresis tracks so as to form a sheath flow flowing in the axial direction of said capillary electrophoresis tracks, and said excitation light irradiates said sheath flow region.

13. A capillary array electrophoresis system according to claim 2, wherein said excitation light irradiates said samples passing along a plane substantially parallel to said plane formed by said terminal ends of said plurality of capillary electrophoresis tracks.

14. A capillary array electrophoresis system according to claim 5, wherein said excitation light irradiates said samples passing along a plane substantially parallel to said plane formed by said terminal ends of said plurality of capillary electrophoresis tracks.

15. A capillary array electrophoresis system according to claim 7, wherein said excitation light irradiates said samples passing along a plane substantially parallel to said plane formed by said terminal ends of said plurality of capillary electrophoresis tracks.

16. A capillary array electrophoresis system according to claim 8, wherein said excitation light irradiates said samples passing along a plane substantially parallel to said plane formed by said terminal ends of said plurality of capillary electrophoresis tracks.

17. A capillary array electrophoresis system according to claim 11, wherein said excitation light irradiates said samples passing along a plane substantially parallel to said plane formed by said terminal ends of said plurality of capillary electrophoresis tracks.

18. A capillary array electrophoresis system according to claim 12, wherein said excitation light irradiates said samples passing along a plane substantially parallel to said plane formed by said terminal ends of said plurality of capillary electrophoresis tracks.

19. A capillary array electrophoresis system comprising:
a plurality of capillary array sheets each having a plurality of parallel electrophoresis tracks having end portions which are aligned at selected intervals, and being fixed to a holder, wherein end portions of said plurality of capillary array sheets are stacked one on top of another;
a light source emitting an excitation light which irradiates samples separated by said plurality of capillary electrophoresis tracks; and
a two-dimensional detector for detecting fluorescence emitted from the irradiated samples.

20. A capillary array electrophoresis system according to claim 19, wherein said excitation light irradiates samples eluted into a flow of buffer solution from a plurality of capillaries.

21. A capillary array electrophoresis system according to claim 19, wherein said plurality of capillaries are filled with gel.

22. A capillary array electrophoresis system according to claim 19, wherein the end portions of said plurality of capillaries in a sheet lie on substantially the same plane, and said system further comprises:
apparatus for applying excitation light in parallel with said plane; and
apparatus for forming a two-dimensional fluorescence image from a direction perpendicular to said plane.

23. A capillary array electrophoresis system according to claim 20, wherein the end portions of said plurality of capillaries in a sheet lie on substantially the same plane, and said system further comprises:
apparatus for applying excitation light in parallel with said plane; and
apparatus for forming a two-dimensional fluorescence image from a direction perpendicular to said plane.

24. A capillary array electrophoresis system according to claim 21, wherein the end portions of said plurality of capillaries in a sheet lie on substantially the same plane, and said system further comprises:

apparatus for applying excitation light in parallel with said plane; and apparatus for forming a two-dimensional fluorescence image from direction perpendicular to said plane.

25. A capillary array electrophoresis system according to claim 19, wherein a flow of buffer solution is formed between a plane formed by the end portions of said plurality of capillaries and a plate having small holes or slits to flow the buffer solution out, and said samples eluted into the buffer solution are fluorescently detected.

26. A capillary array electrophoresis system according to claim 20, wherein the flow of buffer solution is formed between a plane formed by the end portions of said plurality of capillaries and a plate having small holes or slits to flow the buffer solution out, and said samples eluted into the buffer solution are fluorescently detected.

27. A capillary array electrophoresis system according to claim 21, wherein a flow of buffer solution is formed between a plane formed by the end portions of said plurality of capillaries and a plate having small holes or slits to flow the buffer solution out, and said samples eluted into the buffer solution are fluorescently detected.

28. A capillary array electrophoresis system according to claim 22, wherein a flow of buffer solution is formed between a plane formed by the end portions of said plurality of capillaries and a plate having small holes or slits to flow the buffer solution out, and said samples eluted into the buffer solution are fluorescently detected.

29. A capillary array electrophoresis system according to claim 19, wherein a buffer solution is caused to flow in the axial direction of said plurality of capillaries so as to form a sheath flow flowing in a direction of the extension of the axes of said capillaries, and said excitation light irradiates said sheath flow.

30. A capillary array electrophoresis system according to claim 20, wherein the buffer solution is caused to flow in the axial direction of said plurality of capillaries so as to form a sheath flow flowing in a direction of the extension of the axes of said capillaries, and said excitation light irradiates said sheath flow.

31. A capillary array electrophoresis system according to claim 21, wherein a buffer solution is caused to flow in the axial direction of said plurality of capillaries so as to form a sheath flow flowing in a direction of the extension of the axes of said capillaries, and said excitation light irradiates said sheath flow.

32. A capillary array electrophoresis system according to claim 22, wherein a buffer solution is caused to flow in the axial direction of said plurality of capillaries so as to form a sheath flow flowing in a direction of the extension of the axes of said capillaries, and said excitation light irradiates said sheath flow.

33. A capillary array electrophoresis system according to claim 25, wherein the buffer solution is caused to flow in the axial direction of said plurality of capillaries so as to form a sheath flow flowing in a direction of the extension of the axes of said capillaries, and said excitation light irradiates said sheath flow.

34. A capillary array electrophoresis system according to claim 19, wherein said excitation light irradiates said samples passing by a plane substantially parallel to a plane formed by the end portions of said plurality of capillaries.

35. A capillary array electrophoresis system according to claim 20, wherein said excitation light irradiates said samples passing by a plane substantially parallel to a plane formed by the end portions of said plurality of capillaries.

36. A capillary array electrophoresis system according to claim 21, wherein said excitation light irradiates said samples passing by a plane substantially parallel to a plane formed by the end portions of said plurality of capillaries.

37. A capillary array electrophoresis system according to claim 22, wherein said excitation light irradiates said samples passing by a plane substantially parallel to a plane formed by the end portions of said plurality of capillaries.

38. A capillary array electrophoresis system according to claim 25, wherein said excitation light irradiates said samples passing by a plane substantially parallel to a plane formed by the end portions of said plurality of capillaries.

39. A capillary array electrophoresis system comprising:

an optical cell including a buffer solution inlet, a buffer solution outlet, and an optical window in contact with a buffer solution;

a plurality of capillary array sheets each having a plurality of capillaries having end portions which are aligned at selected intervals, and being fixed to a holder;

a light source emitting an excitation light; and a fluorescence detecting system, wherein said capillary array sheets are stacked in such a manner that said end portions of capillaries of said capillary array sheets face said optical window, a buffer solution flows in a space between said end portions of said capillaries and said optical window which is disposed in a direction perpendicular to the stack of said capillary array sheets, wherein said excitation light is introduced from a direction in parallel to the edge of a capillary array sheet in such a manner as to cross a sheath flow of said buffer solution, and wherein said fluorescence detecting system detects fluorescence emitted from a sample by a two-dimensional detector through said optical window of said optical cell.

40. A capillary array electrophoresis system comprising:

an optical cell including a buffer solution, and an optical window in contact with said buffer solution;

a plurality of capillary array sheets each having a plurality of capillaries on which end portions of capillaries in each capillary sheet are aligned at selected intervals and claimed by an upper holder and a lower holder;

an excitation light irradiation system; and a fluorescence detecting system, wherein said capillary array sheets are stacked one on top of another to face said optical window, each of said upper and lower holders of said capillary array sheets has a flat end surface and an edge portion protruding from said end surface and has a buffer solution flow path opening to said flat end surface, wherein said edge portions of said holders are in contact with said optical window and define a space separated for each of said capillary array sheets, wherein said excitation light irradiation system applies excitation light to said space separated for each of said capillary array sheets, and wherein said fluorescence detecting system detects fluorescence emitted from a sample by a two-dimensional detector through said optical window of said optical cell.

41. A capillary array electrophoresis system according to claim 40, wherein said opening in said flat end surface of said buffer solution flow path of said upper holder is positioned on a substantial intermediate line of adjacent capillaries.

42. A capillary array electrophoresis system comprising:

an optical cell including a buffer solution inlet, a buffer solution outlet, a partition member having a plurality of parallel slits and being disposed between said buffer solution inlet and said buffer solution outlet, and an optical window disposed substantially parallel to said partition member at a selected distance in contact with a buffer solution;

a plurality of capillary array sheets each having a plurality of capillaries on which end portions of capillaries in each capillary sheet are aligned at selected intervals and fixed to a holder;

an excitation light irradiation system; and a fluorescence detecting system, wherein said capillary array sheet are stacked one on top of another while distal end of said capillaries are inserted into said slits of said partition member, wherein a buffer solution flows from said buffer solution inlet in the axial direction of said capillaries through said slits of said partition member, then passes through a space between said partition member and said optical window and is discharged from said buffer solution outlet, wherein said excitation light irradiation system applies excitation light in a direction of said slits of said partition member, and wherein said fluorescence detecting system detects fluorescence emitted from a sample by a two-dimensional detector through said optical window of said optical cell.

43. A capillary array electrophoresis system according to claim 42, wherein said excitation light passes through said slits of said partition member.

44. A capillary array electrophoresis system according to claim 42, wherein the capillaries of each of said capillary array sheets are clamped by an upper holder and a lower holder each having grooves for causing said buffer solution to flow along the surface thereof, and distal end portions of said upper and lower holders are fitted into said slits of said partition member.

45. A capillary array electrophoresis system comprising:

a plurality of capillary array sheets each having arranged in a single row a plurality of capillary electrophoresis tracks, wherein terminal ends of said plurality of capillary array sheets are stacked one on top of another;

a light source emitting an excitation light which irradiates samples near said terminal ends; and a two-dimensional detector for detecting fluorescence emitted from said samples;

wherein said samples are eluted into a flow of buffer solution and said excitation light irradiates said samples eluted in said buffer solution, and wherein the flow of said buffer solution is formed between a plane formed by said terminal ends of said plurality of capillary electrophoresis tracks and a plate which is disposed opposite said plane, said plate having small holes or slits to permit the flow of said buffer solution from said terminal ends into said small holes or slits, wherein said samples are eluted into said buffer solution and are fluorescently detected.

46. A capillary array electrophoresis system comprising:

a plurality of capillary array sheets each having arranged in a single row a plurality of capillary electrophoresis tracks, wherein terminal ends of said plurality of capillary array sheets are stacked one on top of another, and said terminal ends of said plurality of capillary electrophoresis tracks of each capillary array sheet lie on substantially the same plane;

means for irradiating samples with an excitation light in parallel with said plane near said terminal ends;

means for forming a two-dimensional fluorescence image from a direction perpendicular to said plane; and a two-dimensional detector for detecting said two-dimensional fluorescence image;

wherein said samples are eluted into a flow of buffer solution and said excitation light irradiates said samples eluted in said buffer solution, and wherein the flow of said buffer solution is formed between a plane formed by said terminal ends of said plurality of capillary electrophoresis tracks and a plate which is disposed opposite said plane, said plate having small holes or slits to permit the flow of said buffer solution from around said terminal ends into said small holes or slits, wherein said samples are eluted into said buffer solution, are fluorescently detected, and then flow out from the small holes or slits.

47. A capillary array electrophoresis system according to claim 45, wherein said buffer solution is caused to flow in an axial direction of said plurality of capillary electrophoresis tracks so as to form a sheath flow flowing in the axial direction of said capillary electrophoresis tracks, and said excitation light irradiates said sheath flow region.

48. A capillary array electrophoresis system according to claim 46, wherein said buffer solution is caused to flow in an axial direction of said plurality of capillary electrophoresis tracks so as to form a sheath flow flowing in the axial direction of said capillary electrophoresis tracks, and said excitation light irradiates said sheath flow region.

49. A capillary array electrophoresis system according to claim 45, wherein said excitation light irradiates said samples passing along a plane substantially parallel to said plane formed by said terminal ends of said plurality of capillary electrophoresis tracks.

50. A capillary array electrophoresis system according to claim 46, wherein said excitation light irradiates said samples passing along a plane substantially parallel to said plane formed by said terminal ends of said plurality of capillary electrophoresis tracks.

51. A capillary array electrophoresis system according to claim 47, wherein said excitation light irradiates said samples passing along a plane substantially parallel to said plane formed by said terminal ends of said plurality of capillary electrophoresis tracks.

52. A capillary array electrophoresis system according to claim 48, wherein said excitation light irradiates said samples passing along a plane substantially parallel to said plane formed by said terminal ends of said plurality of capillary electrophoresis tracks.

53. A capillary array electrophoresis system comprising:

a plurality of capillary array sheets each having a plurality of parallel electrophoresis tracks, wherein end portions of said plurality of capillary array sheets are stacked one on top of another;

a light source emitting an excitation light which irradiates samples separated by said plurality of capillary electrophoresis tracks; and a two-dimensional detector for detecting fluorescence emitted from the irradiated said samples;

wherein a flow of buffer solution is formed between a plane formed by the end portions of said plurality of capillaries and a plate having small holes or slits to flow buffer solution out, and said samples eluted into the buffer solution are fluorescently detected.

54. A capillary array electrophoresis system comprising:

a plurality of capillary array sheets each having a plurality of parallel electrophoresis tracks, wherein end portions of said plurality of capillary array sheets are stacked one on top of another;

a light source emitting an excitation light which irradiates sample separated by said plurality of capillary electrophoresis tracks, wherein said excitation light irradiates samples eluted into a flow of buffer solution form a plurality of capillaries; and a two-dimensional detector for detecting fluorescence emitted from the irradiated samples;

wherein the flow buffer solution is formed between a plane formed by the end portions of said plurality of capillaries and a plate having small holes or slits to flow the buffer solution out, and said samples eluted into the buffer solution are flourescently detected.

55. A capillary array electrophoresis system comprising:

a plurality of capillary array sheets each having a plurality of parallel electrophoresis tracks, wherein end portions of said plurality of capillary array sheets are stacked on top of another, and said plurality of capillaries are filled with gel;

a light source emitting an excitation light which irradiates samples separated by said plurality of capillary electrophoresis tracks; and a two-dimensional detector for detecting fluorescence emitted from the irradiated samples;

wherein a flow of buffer solution is formed between a plane formed by the end portion of said plurality of capillaries and a plate having small holes or slits to flow the buffer solution out, and said samples eluted into the buffer solution are fluorescently detected.

56. A capillary array electrophoresis system comprising:

a plurality of capillary array sheets each having a plurality of parallel electrophoresis tracks, wherein end portion of said plurality of capillary array sheets are stacked one on top of another, and the end portions of said plurality of capillaries in a sheet lie on substantially the same plane;

a light source emitting an excitation light which irradiates samples separated by said plurality of capillary electrophoresis tracks;

apparatus for applying the excitation light in parallel with said plane; and apparatus for forming a two-dimensional fluorescence image from a direction perpendicular to said plane;

a two-dimensional detector for detecting said two-dimensional fluorescence image;

wherein a flow of buffer solution is formed between a plane formed by the end portions of said plurality of capillaries and a plate having small holes or slits to flow the buffer solution out, and said samples eluted into the buffer solution are fluorescently detected.

57. A capillary array electrophoresis system according to claim 53, wherein said buffer solution is caused to flow in the axial direction of said plurality of capillaries so as to form a sheath flow flowing in a direction of the extension of the axes of said capillaries, and said excitation light irradiates said sheath flow.

58. A capillary array electrophoresis system according to claim 53, wherein said excitation light irradiates said samples passing by a plane substantially parallel to a plane formed by the end portions of said plurality of capillaries.

* * * * *